United States Patent
Nordrum et al.

(10) Patent No.: US 10,653,725 B2
(45) Date of Patent: May 19, 2020

(54) METHODS FOR IMPROVING HEALTH OF FARMED FISH

(71) Applicants: Aker BioMarine Antarctic AS, Stamsund (NO); Biomar Group, Aarhus C (DK)

(72) Inventors: Sigve Nordrum, Slependen (NO); Harald Takle, Ås (NO); Sven Martin Jørgensen, Ås (NO); Trygve Sigholt, Myre (NO)

(73) Assignees: Aker BioMarine Antarctic AS, Stamsund (NO); Biomar Group, Aarhus C (DK)

(*) Notice: Subject to any disclaimer, the term of this patent is extended or adjusted under 35 U.S.C. 154(b) by 444 days.

(21) Appl. No.: 15/239,259

(22) Filed: Aug. 17, 2016

(65) Prior Publication Data

US 2017/0049824 A1 Feb. 23, 2017

Related U.S. Application Data

(60) Provisional application No. 62/206,006, filed on Aug. 17, 2015.

(51) Int. Cl.

| | |
|---|---|
| *A61K 35/612* | (2015.01) |
| *A23K 10/22* | (2016.01) |
| *A23K 50/80* | (2016.01) |
| *A23K 20/158* | (2016.01) |
| *A61K 9/00* | (2006.01) |
| *A61K 9/16* | (2006.01) |
| *A61K 31/202* | (2006.01) |
| *A23K 40/10* | (2016.01) |

(52) U.S. Cl.
CPC ............ *A61K 35/612* (2013.01); *A23K 10/22* (2016.05); *A23K 20/158* (2016.05); *A23K 40/10* (2016.05); *A23K 50/80* (2016.05); *A61K 9/0056* (2013.01); *A61K 9/16* (2013.01); *A61K 31/202* (2013.01)

(58) Field of Classification Search
CPC .............. A61K 2300/00; A61K 35/612; A61K 31/202; A61K 9/0056; A61K 9/16; A61K 31/685; A61K 31/122; A61K 31/23; A61K 31/683; A61K 31/20; A61K 31/575; A61K 31/215; A61K 31/235; A61K 31/133; A61K 31/198; A61K 31/225; A61K 45/06; A61K 9/0053; A61K 9/48; A61K 9/4825; A61K 9/4858; A23K 10/22; A23K 10/20; A23K 20/158; A23K 20/111; A23K 20/179; A23K 20/26; A23K 40/10; A23K 40/20; A23K 40/225; A23K 50/80; A23K 40/25; A01K 61/10; A23D 9/013; A23G 3/40; A23J 7/00; A23L 17/40; A23L 33/115; A23L 33/00; A23L 33/17; A23L 17/00; A23V 2002/00; C07F 9/103; C11B 3/006; C11B 1/10; C11B 1/06; Y02A 40/81; Y02A 40/818

See application file for complete search history.

(56) References Cited

U.S. PATENT DOCUMENTS

| | | | |
|---|---|---|---|
| 2008/0044487 A1 | 2/2008 | Bruheim et al. | |
| 2015/0343000 A1* | 12/2015 | Nordrum | A61K 35/612 424/538 |

FOREIGN PATENT DOCUMENTS

| | | | |
|---|---|---|---|
| WO | 2008/117062 | 10/2008 | |
| WO | 2011/031166 | 3/2011 | |
| WO | WO-2011031166 A2 * | 3/2011 | ........... A23K 20/158 |
| WO | 2014/070020 | 5/2014 | |

OTHER PUBLICATIONS

Köhler A, Sarkkinen E, Tapola N, Niskanen T, Bruheim I "Bioavailability of fatty acids from krill oil, krill meal and fish oil in healthy subjects—a randomized, single-dose, cross-over trial" Lipids in Health and Disease, Mar. 15, 2015, 14(19), 10 pages; doi 10.1186/s12944-015-0015-4 (Year: 2015).*

International Search Report, Int'l Patent Application No. PCT/IB2016/001382, dated Mar. 10, 2017, (6 pages).

Martinez-Rubio et al. "Effects of functional feeds on the lipid composition, transcriptomic responses and pathology in heart of Atlantic salmon (*Salmo salar* L.) before and after experimental challenge with Piscine Myocarditis Virus (PMCV)", BMC Genomics, Biomed Central Ltd, vol. 15, No. 1, Jun. 11, 2014, p. 462, (20 pages).

Siah et al. "Piscine Reovirus: Genomic and Molecular Phylogenetic Analysis from Farmed and Wild Salmonids Collected on the Canada/US Pacific Coast" PLOS ONE vol. 10, No. 11, Jan. 1, 2015, p. e0141475, (22 pages).

* cited by examiner

*Primary Examiner* — Aaron J Kosar

(74) *Attorney, Agent, or Firm* — Casimir Jones, S.C.; J. Mitchell Jones

(57) ABSTRACT

The present invention provides methods for treating and preventing viral disease in farmed fish. In particular, the present invention relates to compositions and methods for improving heart health in farmed salmon.

16 Claims, 11 Drawing Sheets

METHODS FOR IMPROVING HEALTH OF FARMED FISH

CROSS-REFERENCE TO RELATED APPLICATIONS

This application claims priority to and the benefit of U.S. Provisional Application No. 62/206,006, filed Aug. 17, 2015, which is hereby incorporated by reference in its entirety.

FIELD OF THE INVENTION

The present invention provides methods for treating and preventing viral disease in farmed fish. In particular, the present invention relates to compositions and methods for improving heart health in farmed salmon.

BACKGROUND OF THE INVENTION

Fish consumption is on the increase around the world. According to the National Marine Fisheries Services, the amount of commercially caught fish (fin- and shell-fish), measured as "edible meat" consumed per person in the United States, increased from 11.2 lbs. (~5.08 kg) in 1910 to 16.6 lbs. (~7.53 kg) in 2004. Salmon consumption in the United States increased nine-fold between 1987 and 1999; during that time total European salmon consumption increased more than four times. Between 1992 and 2002, salmon consumption in Japan doubled. There are many reasons for this increase, including competitive pricing, the perception that eating fatty fish is healthy, and a general increase in fish consumption. Atlantic salmon is a good source of protein, with almost 20 grams per 100 gram serving, and is an excellent source of omega-3-fatty acids, which are thought to aid in cardiovascular health.

Heart and skeletal muscle inflammation (HSMI) was detected in Norway at 160 sites in 2011 and 142 sites in 2012 (see Fiskehelserapporten 2012). Mattilsynets rapport "Regionalt tilsynsprosjekt 2011 and is often associated with viral disease such as piscine reovirus. Prosjekt overlevelse fisk" found that HSMI was largest cause of mortality in sea water (13.8) followed by cardiomyopathy syndrome (CMS) (6.4%) and pancreas disease (PD) (2.1%).

Thus, compositions and method for treating and preventing HSMI are needed.

SUMMARY OF THE INVENTION

The present invention provides methods for treating and preventing viral disease in farmed fish. In particular, the present invention relates to compositions and methods for improving heart health in farmed salmon (e.g., in fish infected with a viral disease).

For example, embodiments of the present invention provide a method of improving a parameter of heart health in fish comprising: feeding fish a dietary ration comprising an amount of krill meal effective to improve one or more parameters of heart health in the fish. The present invention is not limited to particular parameters of heart health. Examples include, but are not limited to, one (e.g. 1, 2, 3, 4, 5, or more of) or more of improved cardiac fatty acid composition, improved erythrocyte fatty acid composition, increased rate of growth, increased body mass, increased body length, increased ventricle mass relative to body mass, increased ventricle mass relative to body length, improved swimming capacity, decreased maximum heart rate, or increased thickness of the compact myocardium. In some embodiments, the improved cardiac fatty acid composition and erythrocyte fatty acid composition comprises an increase in levels of linoleic acid (LA, 18:2n-6) and/or alpha-linolenic acid (ALA). In some embodiments, the ration is a pelleted ration. In some embodiments, the ration comprises from about 4% to 15% krill meal. In some embodiments, the ration comprises approximately 150-250 mg/g fatty acids (e.g., 160-240, 170-230, 180-220, or 185-220 mg/g) and approximately 15-35 (e.g., 18-30%, 20-28%, or 23-26%) lipids. In some embodiments, 2-10% (e.g., 2-8%, 3-8%, or 3-7%) of the fatty acids in said ration are EPA and DHA combined. In some embodiments, the ratio of EPA to DHA in the ration is between approximately 0.7 and 1.8 (e.g., 0.7 and 1.6, 0.8 and 1.5, or 0.9 and 1.4). In some embodiments, the fish are infected with a viral disease. In some embodiments, the ration comprises from 30% w/w to 42% w/w lipids (e.g., 31% to 41%, 32% to 40%, or 34% to 38% w/w lipids). In some embodiments, from 3% to 20% (e.g., from 4% to 18%, 8% to 20%, 10% to 20%, 12% to 20%, or 6% to 16%) of the fatty acids in the said ration are EPA and DHA combined.

Additional embodiments provide a method of improving a parameter of heart health in fish comprising: feeding fish a pelleted dietary ration comprising an amount of krill meal effective to improve one or more parameters of heart health quality in said fish, wherein said one or more parameters of heart health are selected from, for example, improved cardiac fatty acid composition, improved erythrocyte fatty acid composition, increased rate of growth, increased body mass, increased body length, increased ventricle mass relative to body mass, increased ventricle mass relative to body length, improved swimming capacity, decreased maximum heart rate, or increased thickness of the compact myocardium.

Further embodiments provide a fish feed comprising krill meal for use in improving a parameter of heart health in fish.

An even further embodiment provide a fish feed comprising krill meal for use in improving a parameter of heart health in fish wherein said one or more parameters of heart health are selected from the group consisting of improved cardiac fatty acid composition, improved erythrocyte fatty acid composition, increased rate of growth, increased body mass, increased body length, increased ventricle mass relative to body mass, increased ventricle mass relative to body length, improved swimming capacity, decreased maximum heart rate, increased thickness of the compact myocardium and combinations thereof.

Further embodiments provide a fish feed comprising krill meal for use in treating and/or preventing viral disease in farmed fish.

Another embodiment provides a fish feed comprising krill meal for use in treating and/or preventing heart disease.

Additional embodiments are described herein.

DETAILED DESCRIPTION OF THE INVENTION

Figure 1:
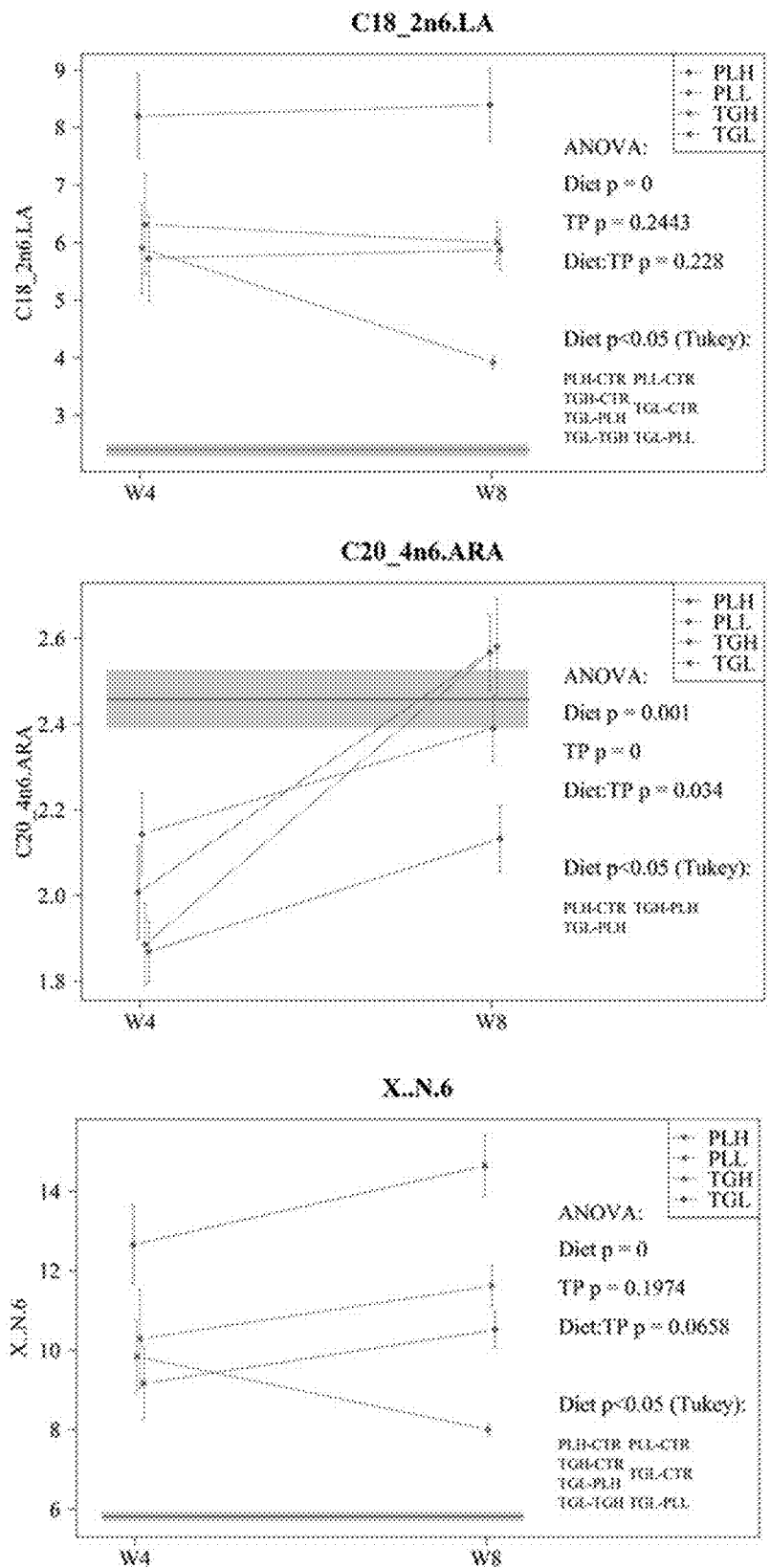
FIG. 1: Selected omega-6 fatty acids in erythrocytes (% of total) from diet groups (n=10) sampled after 4 and 8 weeks. Upper plot: linoleic acid, middle plot: arachidonic acid, lower plot: sum of omega-6 fatty acids. Week 0 levels are shown as a solid grey bar (line=average, grey=standard error). Top right: ANOVA p-values (two-factor with Diet and Time point). Bottom right: Significantly different diets according to Tukey's post-hoc test ($p<0.05$).

The present invention provides methods for treating and preventing viral disease in farmed fish. In particular, the present invention relates to compositions and methods for improving heart health in farmed salmon.

The salmon farming production cycle is about 3 years. During the first year of production the eggs are fertilized and the fish is grown into approximately 100 grams in controlled freshwater environment. Subsequently, the fish is transported into seawater cages where it is grown out to approximately 4-5 kg during a period of 14-24 months. The growth of the fish is heavily dependent on the seawater temperatures, which varies by time of year and across regions. Having reached harvestable size, the fish is transported to primary processing plants where it is slaughtered and gutted.

In the present context the terms "rations" and fish feed is used herein interchangeably.

The present invention provides rations that are useful in treating and/or preventing heart disease (e.g. caused by viral infection or other causes) in salmon. For example, in some embodiments, the present invention provides rations comprising krill meal that improve one or more measures of cardiac health (e.g., including but not limited to, improved cardiac fatty acid composition, improved erythrocyte fatty acid composition, increased rate of growth, increased body mass, increased body length, increased ventricle mass relative to body mass, increased ventricle mass relative to body length, improved swimming capacity, decreased maximum heart rate, or increased thickness of the compact myocardium).

For example, embodiments of the present invention provide a method of improving a parameter of heart health in fish comprising: feeding fish a dietary ration comprising an amount of krill meal effective to improve one or more parameters of heart health in the fish. The present invention is not limited to particular parameters of heart health. Examples include, but are not limited to, one (e.g. 1, 2, 3, 4, 5, or more of) or more of improved cardiac fatty acid composition, improved erythrocyte fatty acid composition, increased rate of growth, increased body mass, increased body length, increased ventricle mass relative to body mass, increased ventricle mass relative to body length, improved swimming capacity, decreased maximum heart rate, or increased thickness of the compact myocardium. By "improve" it is meant that the parameter is improved as compared to the parameter's value in a control animal (e.g., fish) receiving a diet that does not include an effective amount of krill meal.

In some embodiments, the improved cardiac fatty acid composition and erythrocyte fatty acid composition comprises an increase in levels of linoleic acid (LA, 18:2n-6) and/or alpha-linolenic acid (ALA).

Additional embodiments provide a method of improving a parameter of heart health in fish comprising: feeding fish a pelleted dietary ration comprising an amount of krill meal effective to improve one or more parameters of heart health quality in said fish, wherein said one or more parameters of heart health are selected from, for example, improved cardiac fatty acid composition, improved erythrocyte fatty acid composition, increased rate of growth, increased body mass, increased body length, increased ventricle mass relative to body mass, increased ventricle mass relative to body length, improved swimming capacity, decreased maximum heart rate, or increased thickness of the compact myocardium.

Further embodiments provide a fish feed comprising krill meal for use in treating and/or preventing viral disease in farmed fish.

Another embodiment provides a fish feed comprising krill meal for use in treating and/or preventing heart disease.

In an embodiment the heart disease is caused by viral infection. In a further embodiment the fish is salmon.

Typical salmon rations of the invention comprise from about 5% to 50% fish meal, such as 10% to 40%, e.g. 15% to 30%, such as 20% to 25% fish meal, 4% to 15% krill meal, 5% to 30%, vegetable oil, such as 100 to 25%, e.g. 15% to 20%; vegetable oil and 5%-15% fish oil, such as 6%-14%, e.g. 7%-13%, such as 8%-12%, e.g. 9%-11%, such as 10%-12% fish oil, expressed as % weight of component/ weight of the ration (% w/w). In some embodiments, the rations have a crude protein content of from about 32% to 46%, such as 34%-44%, e.g. 36%-40%, preferably from about 36% to 42%, a crude lipid content of from about 26% to 42%, such as 30% to 40%, e.g. 32%-36%, such as 34% to 46%, preferably from about 28% to 38%, a carbohydrate (NFE) content of from about 11% to 18%, such as 12% to 17%, e.g. 14%-16%, such as 11% to 17%, preferably from about 13% to 15%, a fiber content of from about 1% to 5%, such as 2%-4.5%, e.g. 3% to 4%, such as 3.5% to 4% preferably from about 1.5% to 2.5%, an ash content of from about 4% to 7%, such as 5% to 6%, preferably about 4.5% to 6.5%, a total phosphorus content (P) of from about 0.5% to 1.4%, such as 0.7% to 1.3, e.g. 0.8% to 1.2, such as 0.9% to 1.1%, preferably about 0.6% to 1.0%, a gross energy content of from about 20 to 30 MJ/kg, e.g. 21 to 29 MJ/kg, such as 22 to 27 MJ/kg, e.g. 24 to 26 MJ/kg, such as 25 to 26 MJ/kg preferably from about 23 to 28 MJ/kg, and a digestible energy content of from about 20 to 24 MJ/kg, such as 21 to 23 MJ/kg, e.g. 22 to 23 MJ/kg. Typical components of a salmon ration will contain krill meal in amount of about 4 to 15%, e.g. 5 to 14%, such as 6 to 13%, e.g. 5 to 12%, e.g. 7 to 11%, such as 8 to 10%, e.g. 9 to 10%, with the remaining requirements being met by, for example, fish meal, fish oil, vegetable oil (e.g., rapeseed or soybean oil), wheat gluten, wheat, soya cake, sunflower cake, and horse beans. The rations may further be supplemented with vitamins and minerals.

In some preferred embodiments, the ration is a pelleted ration. The pellet sizes may preferably range from about 4 mm to 12 mm, such as 4 mm to 12 mm, 5 mm to 11 mm, 7 mm to 9 mm, 8 mm to 9 mm and most preferably from about 6 mm to 10 mm. In an embodiment the pelleted ration is selected from the group consisting of pressed fish feed, extruded fish feed and wet semi-moist feed.

In some preferred embodiments, the rations comprise krill meal, most preferably from about 1% to 65% w/w krill meal, such as 5% to 64%, e.g. 6% to 63%, such as 7% to 62%, e.g. 8% to 61%, e.g. 9% to 60%, such as 10% to 59%, e.g. 11% to 58%, e.g. 12% to 57%, such as 13% to 56%, e.g. 14% to 55%, e.g. 15% to 54%, such as 16% to 53%, e.g. 17% to 52%, e.g. 18% to 50%, such as 19% to 49%, e.g. 20% to 48%, e.g. 21% to 47%, such as 22% to 46%, e.g. 23% to 45%, e.g. 24% to 44%, such as 25% to 43%, e.g. 26% to 42%, e.g. 27% to 41%, such as 28% to 40%, e.g. 29% to 39%, e.g. 30% to 38%, such as 31% to 37%, e.g. 32% to 36%, e.g. 33% to 35%, such as 34% to 35%, preferably 2% to 40% w/w krill meal, more preferably from about 3% to 30% w/w krill meal, and most preferably about 4% to 150% w/w krill meal, expressed as % weight of krill meal/weight of the ration (% w/w).

In some preferred embodiments, the krill meal is prepared from whole grinded and dried *Euphausia superba*. In some embodiments, the krill meal comprises an antioxidant. In some embodiments, the antioxidant is a synthetic antioxidant. In some embodiments, the synthetic antioxidant is ethoxyquin, and is included in amount of from about 100 to 300 mg/kg, e.g. 110 to 290 mg/kg, such as 120 to 280 mg/kg, e.g. 130 to 270 mg/kg, such as 160 to 260 mg/kg, e.g. 170 to 240 mg/kg, such as 180 to 230 mg/kg, e.g. 190 to 220 mg/kg, such as 200 to 210 mg/kg and preferably from about 150 to 250 mg/kg. In preferred embodiments, the krill meal comprises from about 48% to 68% w/w, e.g. 49% to 67%, such as 50% to 66%, e.g. 51% to 65%, such as 52% to 64%, e.g. 54% to 62%, such as 55% to 61%, e.g. 56% to 60%, such as 57% to 59%, e.g. 58% to 59% and preferably 53% to 63% w/w crude protein, from about 15% to 35% w/w, e.g. 16% to 34%, such as 17% to 33%, e.g. 19% to 32%, such as 20% to 31%, e.g. 21% to 30%, such as 22% to 29%, e.g. 23% to 27%, such as 24% to 26%, e.g. 25% to 27%, preferably 18% to 28% w/w total fat, from about 4% to 80% w/w water, e.g. 5% to 7%, e.g. 6% to 7% water and from about 8% to 14% w/w ash, such as 9% to 13%, e.g. 10% to 12%, such as 11 to 12%, expressed as % weight of component/weight of the meal (% w/w). In some embodiments, the fat comprises from about 30% to 50% w/w, such as e.g. 31% to 49%, such as 32 to 48%, e.g. 33% to 48%, such as 34 to 47%, e.g. 35% to 47%, such as 36% to 46%, e.g. 37% to 45%, such as 38 to 44%, e.g. 39% to 43%, such as 40 to 42%, e.g. 41% to 42%, preferably about 35% to 45% w/w phospholipids, expressed as % weight of phospholipids/weight of the total fat (% w/w). In some embodiments, the fat comprises from about 15% to 31% w/w, e.g. 16% to 30%, such as 17 to 29%, e.g. 18% to 28%, such as 19 to 27%, e.g. 20% to 26%, such as 21 to 250%, e.g. 22% to 24%, such as 23 to 28%, preferably from about 19% to 27% w/w omega-3 fatty acids, expressed as % weight of omega-3 fatty acids/weight of the total fatty acids (% w/w). In some embodiments, the ratio of EPA to DHA fatty acids in the fat is from about 3:1 to 1.5:1, e.g. 2.9:1 to 1.6:1, such as 2.8:1 to 1.7:1, 2.7:1 to 1.8:1, 2.6:1 to 1.9:1, 2.5:1 to 2.0:1, 2.4:1 to 2.1:1, 2.3:1 to 2.2:1, 2.4:1 to 2.0:1 and preferably from about 2.5:1 to 1.8:1.

In some embodiments, the ration comprises approximately 150-250 mg/g fatty acids (e.g., 155-245, 160-240, 165-235, 170-230, 175-225, 180-220, 185-220, 190-215, 195-210, 200-205 mg/g,) and approximately 15-35 (e.g., 16-34%, 17-33%, 18-32%, 19-31%, 20-30%, 21-29%, 22-28%, 23-27%, 24-26%, 25-26%, 18-30%, 20-28%, or 23-26%) lipids. In some embodiments, 2-10% (e.g., 3-9%, 4-8%, 5-7%, 6-7%, 2-8%, 3-8%, or 3-7%) of the fatty acids in said ration are EPA and DHA combined. In some embodiments, the ratio of EPA to DHA in the ration is between approximately 0.7 and 1.8 (e.g., 0.8 and 1.7, 0.9 and 1.6, 1.0 and 1.5, 0.9 and 1.4, 1.0 and 1.3, 1.1 and 1.2, 0.7 and 1.6, 0.8 and 1.5, or 0.9 and 1.4).

In some embodiments, the ration comprises from 30% w/w to 42% w/w lipids (e.g., 31% to 41%, 32% to 40%, or 34% to 38% w/w lipids). In some embodiments, from 3% to 20% (e.g., from 4% to 18%, 8% to 20%, 10% to 20%, 12% to 20%, or 6% to 16%) of the fatty acids in the said ration are EPA and DHA combined.

In preferred embodiments, the rations are provided to an animal in need thereof (e.g., fish in an aquaculture operation) in an amount consistent with the normal daily diet for the stage of growth for the animal. For example, if the animal is an aquacultured fish, the amount of the ration provided will provide the required daily nutrients in terms of, e.g., energy, protein, fat, carbohydrates, minerals, vitamins, etc., for the fish's stage of growth or life cycle, e.g., fry, parr, first year smolt, transfer and adult salmon.

EXPERIMENTAL

Feed Composition

All groups were fed the same primer diet for 4 weeks prior to start of experiment. Four test diets were then introduced, with proximate and lipid composition given in Table 1. The TGH (triglyceride high) diet was reformulated twice according to analysis of lipid composition after start of experiment. Accordingly, this group changed diet twice during the experiment, with the final TGH4 diet fed shortly after the intermediate sampling until termination of experiment. The PLL2 (phospholipid low) diet is referred to as PLLt.

TABLE 1a

Percentage fatty acid composition of test diets. TGH: triglyceride high EPA/DHA, TGL: triglyceride low EPA/DHA, PLH: phospholipid high EPA/DHA, PLL: phospholipid low EPA/DHA.

| | Diet code | | | | | |
|---|---|---|---|---|---|---|
| Nofima | | 1 | | 3 | 2 | 3 |
| analysis | TGH2 | TGH3 | TGH4 | TGL | PLH | PLL2 |
| Total fatty acids (mg/g) | 186.18 | 178.23 | 219.28 | 190.4 | 199.05 | 185.65 |
| Lipid % (Folch) | 23.86 | 23.39 | 24.9 | 23.58 | 25.64 | 23.29 |
| EPA | 2.6 | 2.9 | 3.6 | 1.6 | 4.2 | 1.6 |
| DHA | 2.6 | 3.2 | 3.4 | 1.7 | 3.1 | 1.5 |
| Sum EPA, DHA (% FA) | 5.2 | 6.0 | 7.0 | 3.2 | 7.3 | 3.1 |
| ARA | 0.2 | 0.2 | 0.2 | 0.1 | 0.2 | 0.2 |
| n-3 | 13.5 | 14.6 | 7.8 | 11.8 | 15.3 | 11.8 |
| n-6 | 24.9 | 20.5 | 19.6 | 24.3 | 20.1 | 24.3 |
| n-0 | 13.6 | 13 | 13.5 | 12.9 | 16.5 | 12.9 |
| Ratio EPA/DHA | 1.0 | 0.9 | 1.0 | 0.9 | 1.4 | 1.0 |
| Ratio EPA/ARA | 14.7 | 13.1 | 14.9 | 13.7 | 25.4 | 8.7 |
| n-3/n-6 | 0.54 | 0.71 | 0.40 | 0.48 | 0.76 | 0.48 |
| Target fat (%) | 23.203 | 23.22 | 23.06 | 22.84 | 23.45 | 23.16 |
| Target EPA, DHA (% of FA) | 4.06 | 5.22 | 7.2 | 2.5 | 4.25 | 2.63 |

TABLE 1b

Proximate composition of test diets (% of dry weight).

| TC analysis | TGH2 | TGH3 | TGH4 | TGL | PLH | PLL2 |
|---|---|---|---|---|---|---|
| Protein | 46.9 | 48.3 | 47.0 | 46.2 | 47.6 | 45.8 |
| Fat | 22.4 | 22.3 | 23.9 | 21.6 | 24.4 | 21.7 |
| Water | 5.8 | 4.0 | 5.5 | 6.5 | 6.0 | 6.1 |
| Ash | 6.6 | 6.5 | 6.3 | 5.9 | 7.7 | 6.2 |
| GE(MJ/kg) | 22.8 | 22.0 | 22.7 | 22.8 | 23.4 | 22.6 |

The time line of the experiment is in Table 2. Intermediate sampling was scheduled 4 and not 3 weeks after introduction of test feeds, thus in the remaining sections of the example, week 4 actually is week 3.

TABLE 2

| Time line of experiment | | | |
|---|---|---|---|
| Event | Week (expt) | Days (expt) | Date (2014) |
| Start primer feed | −4 | −27 | 15.8 |
| Start test feeds | 0 | 0 | 11.9 |
| Shift TGH2 to TGH3 | 2 | 11 | 22.9 |
| Intermediate sampling | 3 | 21 | 2.10 |
| Shift TGH3 to TGH4 | 4 | 27 | 8.10 |
| Swim test | 8 | 53-55 | 3-5.11 |
| Heart rate test | 8 | 54-56 | 4-6.11 |
| End sampling | 8 | 55 | 5.11 |

Fatty Acid Analysis
Heart

The dietary effects on cardiac fatty acid composition (Table 3) were evaluated in 10 fish (one fish excluded for PLH) per diet group (5 fish per tank) sampled after 8 weeks feeding (end sampling), and compared with time zero ('CTR', time zero after four weeks feeding with priming diet). Complete data is in Appendix 1.

A general trend was the different levels between time zero (CTR in Table 3) and end point (week 8) for all diets. Most pronounced was a 95-175% increase in linoleic acid (LA, 18:2n-6) and 81-108% increase in alpha-linolenic acid (ALA, 18:3n-3), the precursors of ARA, EPA and DHA. Levels of EPA and DHA also decreased in all diets. Levels of ARA decreased in PLH but were unchanged in the other diets. This also resulted in reduced ratios of EPA/DHA, EPA/ARA and n-3/n-6 in all diets from time zero, except for PLH, which had similar EPA/DHA and EPA/ARA ratios.

TABLE 3

Fatty acid composition of heart ventricles (% of total) from fish prior to start (CTR, week 0) and after 8 weeks feeding the test diets (PLH, PLL, TGH, TGL). Relevant fatty acids and sums/ratios are selected and given as average levels ± SEM. Diets with different letters are significantly different from each other (post-hoc pairwise comparisons with Tukey's test, $p < 0.05$). Underscore means CTR (after priming diet week 0) is different from all other test diets without differences between the diets.

| | CTR | | PLH | | PLL | | TGH | | TGL | |
|---|---|---|---|---|---|---|---|---|---|---|
| | Aver | SEM | Aver | SEM | Aver | SEM | Aver | SEM | Aver | SEM |
| C 18:2 n-6 | 4.77$^a$ | 0.14 | 12.48$^{bc}$ | 0.48 | 11.25$^b$ | 0.35 | 9.32$^d$ | 0.38 | 13.14$^c$ | 0.40 |
| C 18:3 n-6 | 0.16$^a$ | 0.00 | 0.08$^b$ | 0.01 | 0.06$^c$ | 0.00 | 0.08$^b$ | 0.01 | 0.07$^{bc}$ | 0.00 |
| C 18:3 n-3 | 1.57 | 0.02 | 2.89 | 0.11 | 3.14 | 0.13 | 3.27 | 0.14 | 2.84 | 0.10 |
| C 20:4 n-3 | 0.14 | 0.00 | 0.08 | 0.01 | 0.08 | 0.00 | 0.07 | 0.01 | 0.06 | 0.01 |
| C 20:3 n-6 | 0.30$^a$ | 0.01 | 0.74$^b$ | 0.05 | 1.48$^c$ | 0.05 | 0.59$^b$ | 0.02 | 1.64$^c$ | 0.08 |
| C 20:4 n-6 | 1.82$^{ab}$ | 0.03 | 1.20$^c$ | 0.06 | 1.78$^{ab}$ | 0.16 | 1.46$^{ac}$ | 0.07 | 2.10$^b$ | 0.10 |
| C 20:3 n-3 | 0.11$^a$ | 0.00 | 0.21$^{ab}$ | 0.01 | 0.21$^{ab}$ | 0.01 | 0.26$^b$ | 0.01 | 0.27$^b$ | 0.07 |
| C 20:5 n-3 | 8.40$^a$ | 0.23 | 6.06$^b$ | 0.29 | 4.88$^c$ | 0.12 | 5.84$^{bd}$ | 0.23 | 5.08$^{cd}$ | 0.14 |
| C 22:4 n-6 | 0.17 | 0.01 | 0.11 | 0.02 | 0.10 | 0.00 | 0.10 | 0.00 | 0.12 | 0.01 |
| C 22:5 n-3 | 2.63$^a$ | 0.03 | 1.49$^{bc}$ | 0.05 | 1.45$^b$ | 0.05 | 1.73$^d$ | 0.06 | 1.64$^{cd}$ | 0.04 |

TABLE 3-continued

Fatty acid composition of heart ventricles (% of total) from fish prior to start (CTR, week 0) and after 8 weeks feeding the test diets (PLH, PLL, TGH, TGL). Relevant fatty acids and sums/ratios are selected and given as average levels ± SEM. Diets with different letters are significantly different from each other (post-hoc pairwise comparisons with Tukey's test, p < 0.05). Underscore means CTR (after priming diet week 0) is different from all other test diets without differences between the diets.

|  | CTR | | PLH | | PLL | | TGH | | TGL | |
| --- | --- | --- | --- | --- | --- | --- | --- | --- | --- | --- |
|  | Aver | SEM | Aver | SEM | Aver | SEM | Aver | SEM | Aver | SEM |
| C 22:6 n-3 | 33.51 | 0.26 | 25.37 | 1.54 | 26.90 | 0.73 | 28.09 | 1.21 | 27.49 | 0.88 |
| Σ EPA + DHA | 41.91 | 0.45 | 31.44 | 1.82 | 31.78 | 0.81 | 33.93 | 1.40 | 32.57 | 0.99 |
| Σ N-3 | 46.64 | 0.44 | 36.30 | 1.73 | 36.89 | 0.78 | 39.44 | 1.33 | 37.81 | 1.00 |
| Σ N-6 | $7.56^a$ | 0.12 | $15.54^b$ | 0.42 | $15.54^b$ | 0.20 | $12.28^c$ | 0.30 | $18.02^d$ | 0.29 |
| Rat EPA/DHA | $0.25^a$ | 0.01 | $0.24^a$ | 0.01 | $0.18^b$ | 0.00 | $0.21^c$ | 0.01 | $0.18^b$ | 0.00 |
| Rat EPA/ARA | $4.62^a$ | 0.08 | $5.04^a$ | 0.10 | $2.74^b$ | 0.16 | $3.99^c$ | 0.12 | $2.42^b$ | 0.10 |
| Ratio N-3/N-6 | $6.17^a$ | 0.15 | $2.34^b$ | 0.17 | $2.37^b$ | 0.08 | $3.21^{cd}$ | 0.17 | $2.10^b$ | 0.08 |

Between diets, levels of EPA generally reflected the composition of the diets, with highest levels in PLH and TGH (not statistically different from TGL). In contrast, DHA levels were similar in all diets and thus did not reflect the dietary input. This resulted in similar sum of EPA+DHA for all diets. However, the ratios of EPA/DHA and EPA/ARA were highest in PLH, higher than TGH which again was higher that PLL and TGL.

Blood Erythrocytes

The dietary effects on erythrocyte fatty acid composition (FIGS. 1-4) were evaluated in 10 fish per diet group (5 fish per tank) sampled after 4 and 8 weeks feeding (end sampling), and compared with time zero (after 4 weeks of feeding with priming diet).

Figure 2:
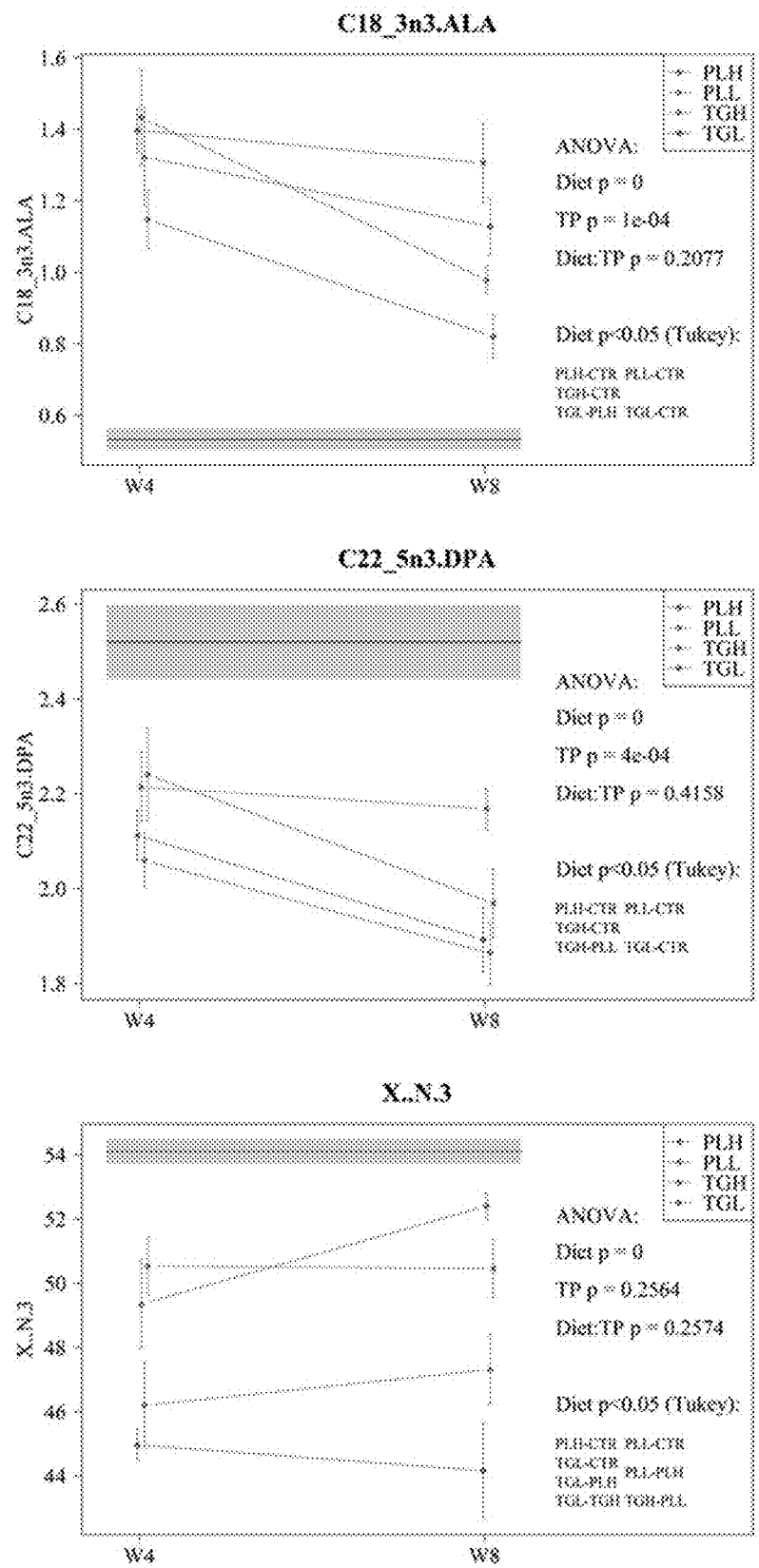
FIG. 2: Selected omega-3 fatty acids in erythrocytes (% of total) from diet groups (n=10) sampled after 4 and 8 weeks. Upper plot: alpha-linolenic acid, middle plot: docosapentaenoic acid, lower plot: sum of omega-3 fatty acids. Week 0 levels are shown as a solid grey bar (line=average, grey=standard error). Top right: ANOVA p-values (two-factor with Diet and Time point). Bottom right: Significantly different diets according to Tukey's post-hoc test (p<0.05).
Figure 3:
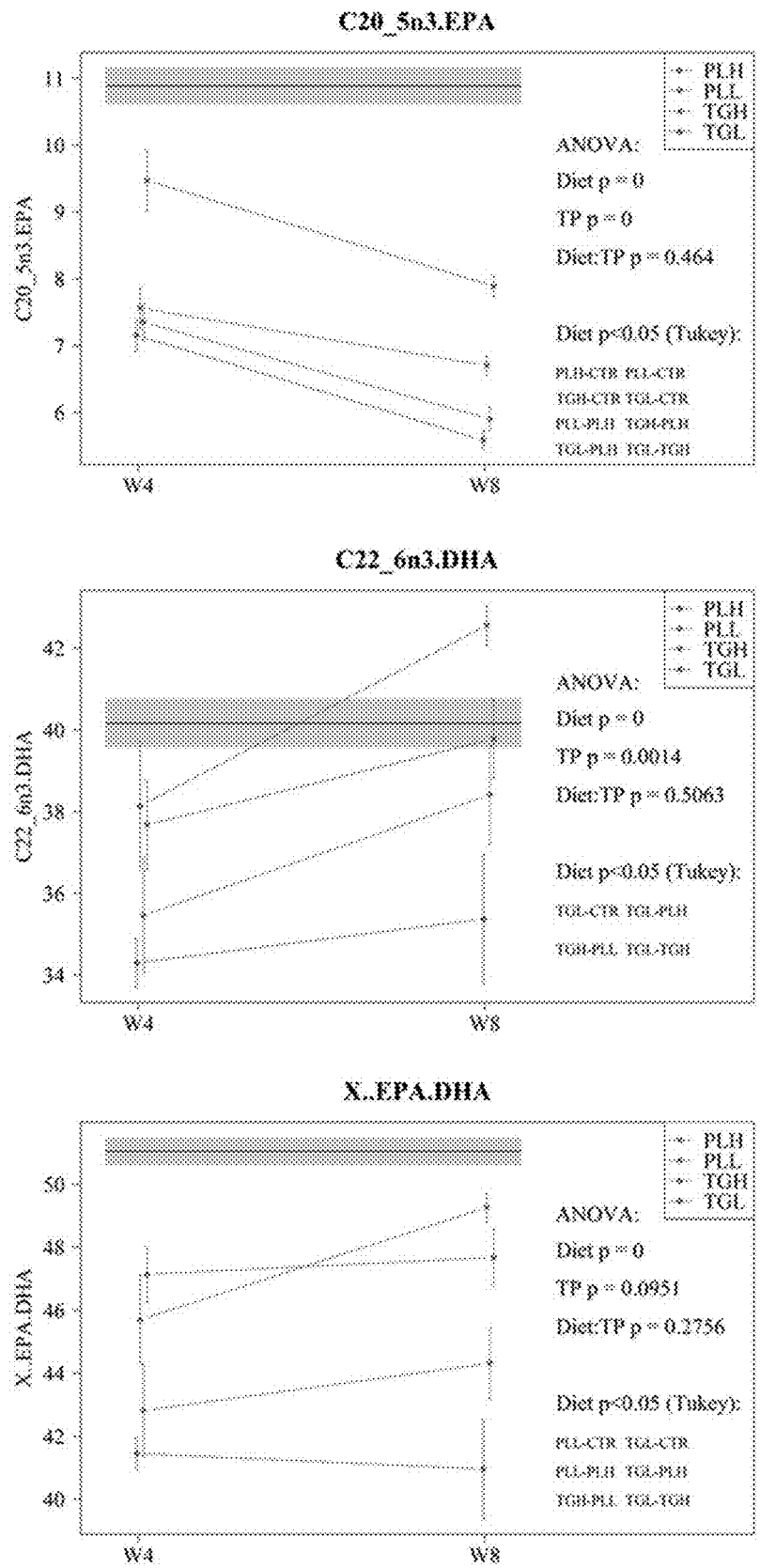
FIG. 3: Selected omega-3 fatty acids in erythrocytes (% of total) from diet groups (n=10) sampled after 4 and 8 weeks. Upper plot: Eicosapentaenoic acid, middle plot: Docosahexaenoic acid, lower plot: Sum of EPA and DHA. Week 0 levels are shown as a solid grey bar (line=average, grey=standard error). Top right: ANOVA p-values (two-factor with Diet and Time point). Bottom right: Significantly different diets according to Tukey's post-hoc test (p<0.05).
Figure 4:
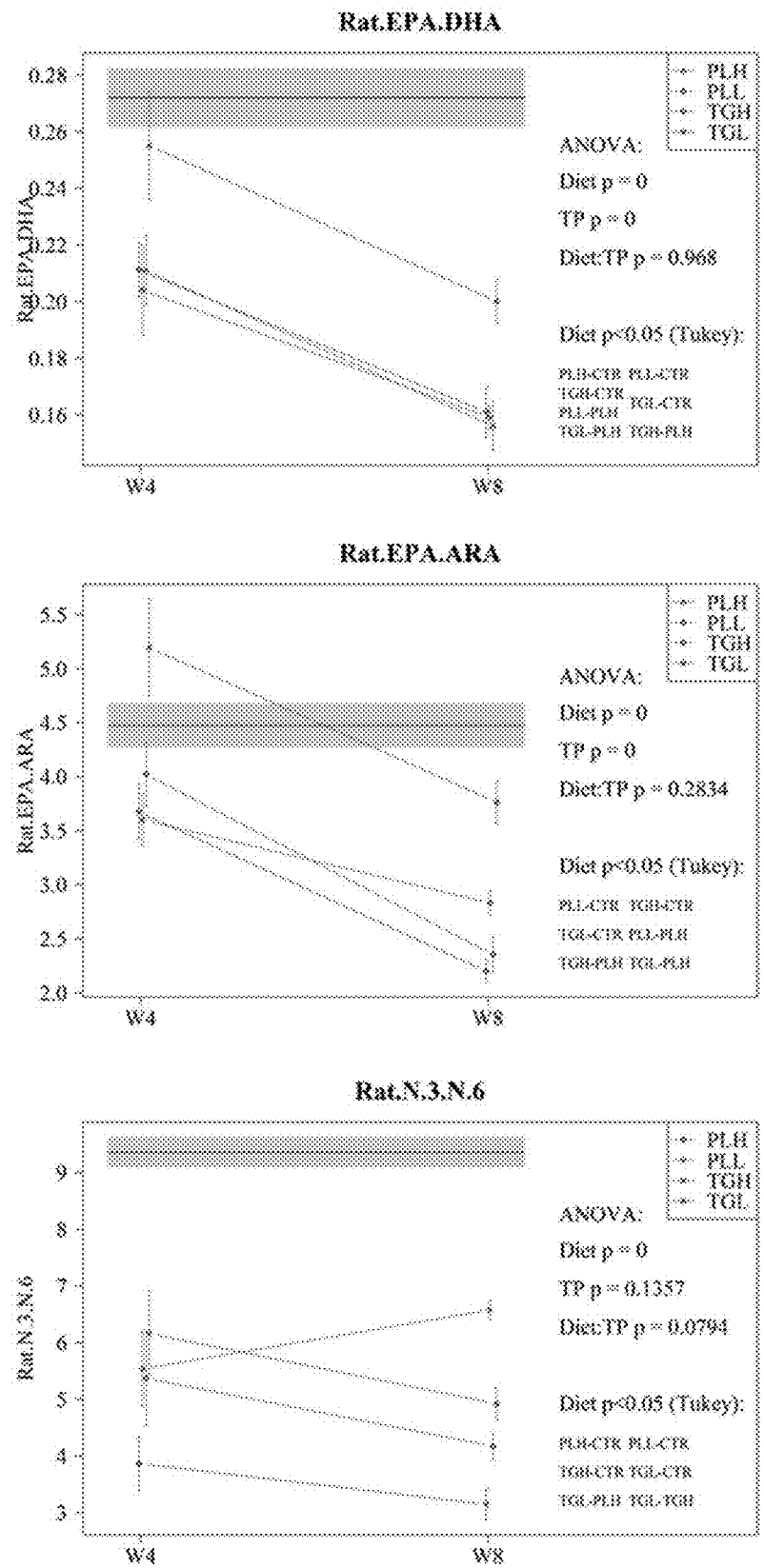
FIG. 4: Selected ratios of fatty acids in erythrocytes (% of total) from diet groups (n=10) sampled after 4 and 8 weeks. Upper plot: EPA/DHA ratio, middle plot: EPA/ARA ratio, lower plot: n-3/n-6 ratio. Week 0 levels are shown as a solid grey bar (line=average, grey=standard error). Top right: ANOVA p-values (two-factor with Diet and Time point). Bottom right: Significantly different diets according to Tukey's post-hoc test (p<0.05).

Similar to the heart fatty acids, levels of the long-chained PUFA precursors ALA and LA increased from time zero (FIGS. 1 and 2). ARA were lower in all diets after 4 weeks but increased to similar levels after 8 weeks, except for PLH still being lower (p=0.08, FIG. 1), similar to heart after 8 weeks. EPA also decreased gradually and significantly from start until week 8 (FIG. 3). In contrast to the heart, DHA levels were generally maintained after start (except reduced levels in TGL at 4 weeks), and gradually increased (numerically) in all diets until 8 weeks (FIG. 3). However, reducing ratios of EPA/DHA and EPA/ARA were observed for all diets from time zero, while n-3/n-6 ratios remained unchanged but significantly lower compared to start at both time points (FIG. 4).

Between diets. EPA were higher in PLH compared to the other diets at both time points (except for similar to TGH at 8 weeks). PLL, TGL and TGH had similar levels at both time points. For DHA, all diets had similar levels at both time points, except for TGH (numerically highest among all at 8 weeks) being higher than TGL (lowest at 8 weeks). The EPA/DHA and EPA/ARA ratio was higher in PLH compared to the other diets, which were similar (FIG. 4).

Growth and Recovery Tests

Figure 5:
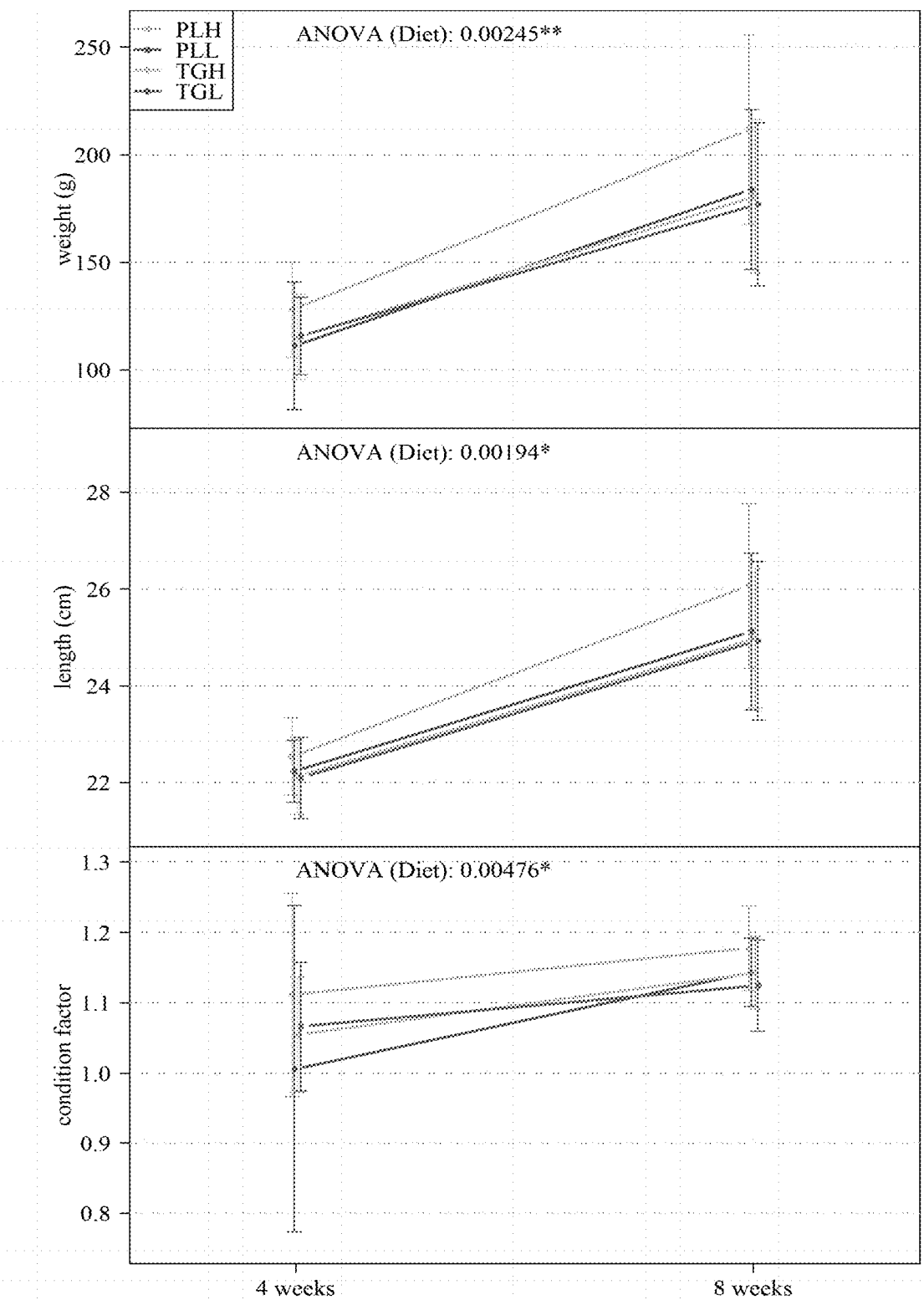
FIG. 5: Average body mass, fork length and condition factor of each diet group after 4 and 8 weeks. Data are average values (n=20)±SEM. ANOVA results are indicated on top of each plot.

Weight and length was recorded for 20 fish per diet groups at the intermediate and end-point sampling. FIG. 5 shows that PLH was bigger than the other groups and this difference was increasing from week 4 to week 8 (week 4: PLH weight average+12.2% than other groups, length+1.7%; week 8: PLH weight average+17.2% than other groups, length+4.2%). PLH also had higher condition factor compared to the other diets.

Organ Indices

Figure 6:
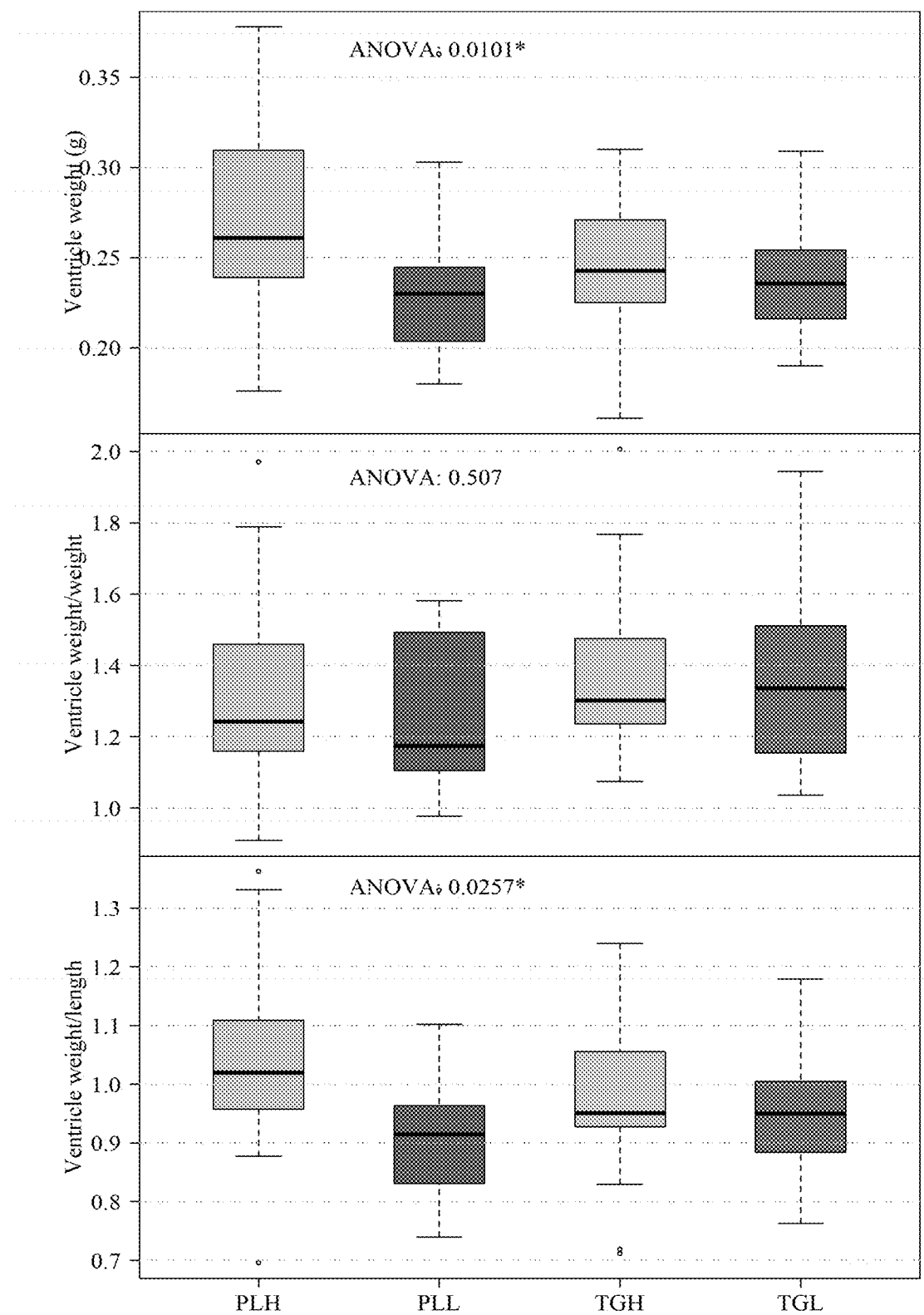
FIG. 6: Relative ventricle mass of diet groups after 8 weeks. Boxes show median values (n=20, solid line) with 25 and 75 percentiles. ANOVA results are indicated on top of each plot.

Ventricle weight was measured for fish sampled at the end point and calculated relative to body mass and length. FIG. 6 shows that PLH had larger ventricles than the other groups, as expected given their higher body mass (see Section 5). Correspondingly, ventricle mass relative to body mass was not different to the other groups. However, ventricle mass relative to body length was significantly higher for PLH in comparison to the other groups.

Swimming Capacity

Figure 7:
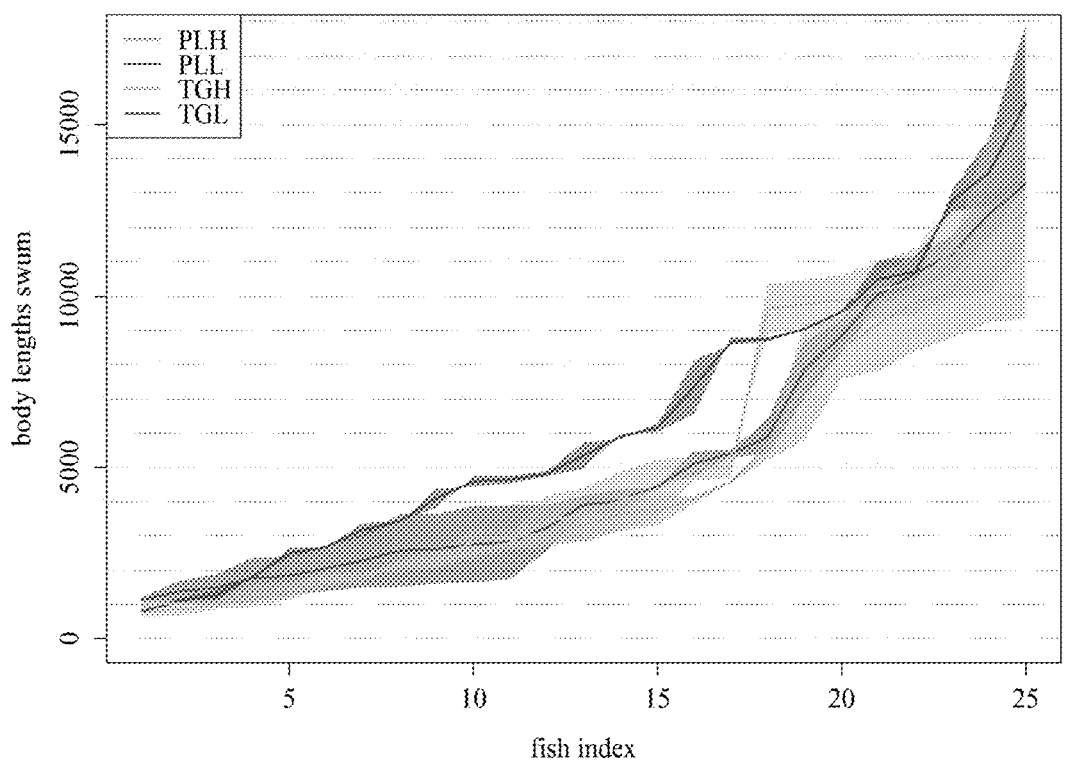
FIG. 7: Sorted numbers of body length swum until exhaustion for the 25 fish in each run. Solid lines mark the average between duplicate runs for each group. Shaded areas under the solid lines indicate results from the two replicate runs.

Fifty fish per diet group was tested for swimming capacity (in duplicate runs per group, n=25) at the end point, and evaluated by calculating the number of body lengths swum until exhaustion for each fish by dividing the total distance swum in the tunnel (water speed×time swum) by the body length of the respective fish. Fish were sorted according to this number for plotting ("fish index", FIG. 7).

Results from the replicate run for each group (FIG. 7) show high differences between the weaker swimmers of the TGL group and the stronger swimmers of the PLH groups. In contrast, very low variation was observed for the PLL replicates. Group TGH separated into 17 weaker fish (swum <5000 body lengths) and 8 stronger fish (swum >9000 body lengths). This separation occurred in both replicate round.

Figure 8:
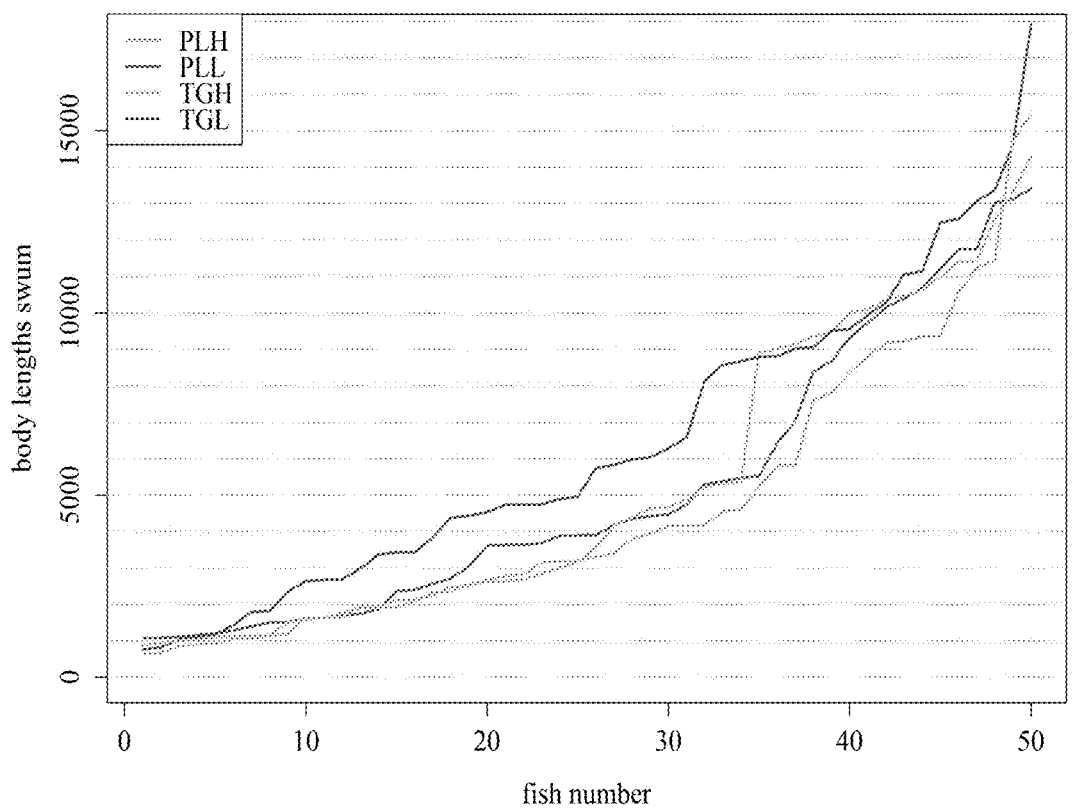
FIG. 8: Sorted numbers of body length swum until exhaustion for the 50 fish in both duplicate runs.

When combining data from replicate runs (50 fish per group in total), it seems that among the weaker swimmers (<8500 BL) of all groups the PLL group were performing better than the rest (FIG. 8). Among the strongest swimmers of all groups differences were minor, but tentatively poorer capacity of PLH.

Figure 9:
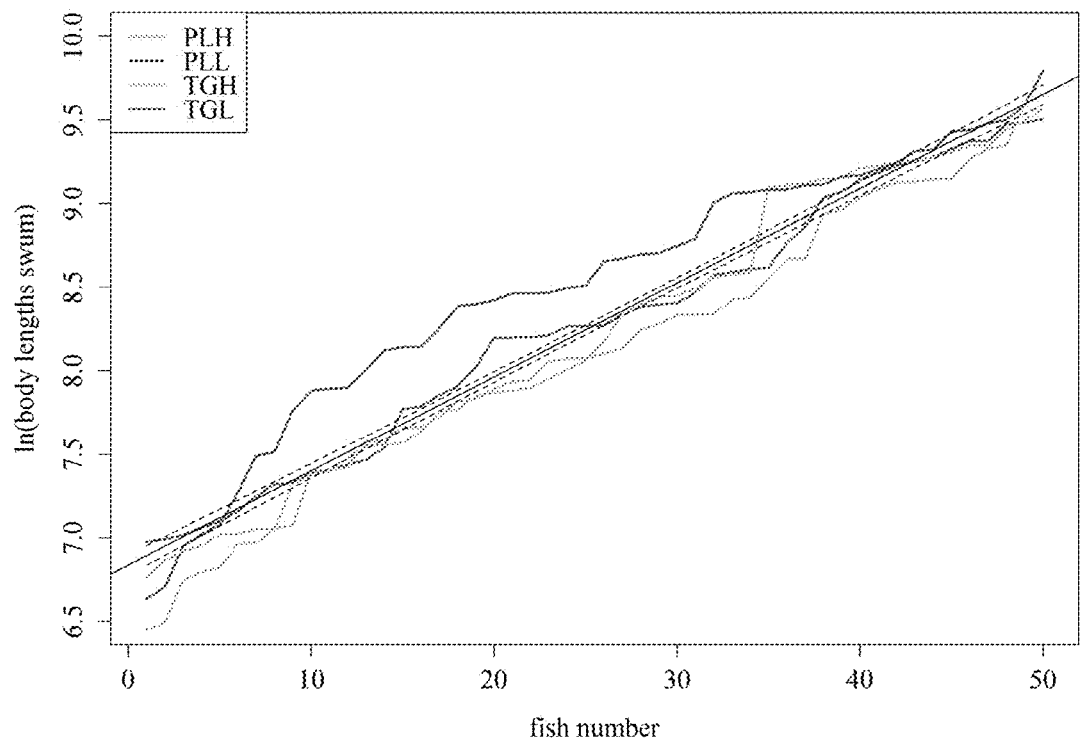
FIG. 9: Same numbers as in FIG. 8 but numbers were logarithm transformed. The linear regression model for all four groups is shown as a black line.

The curves of the swimming capacity resembled an exponential function; thus, values were ln-transformed for linear regression (FIG. 9). The different shape of PLL group becomes more apparent in this Figure, with PLH, TGH and TGL being close to linearity, but PLL being right-curved. This shows that the PLL curve (in its non-logarithmic form) is closer to a straight line than the other three groups (which are exponential).

Heart Physiology

Figure 10:
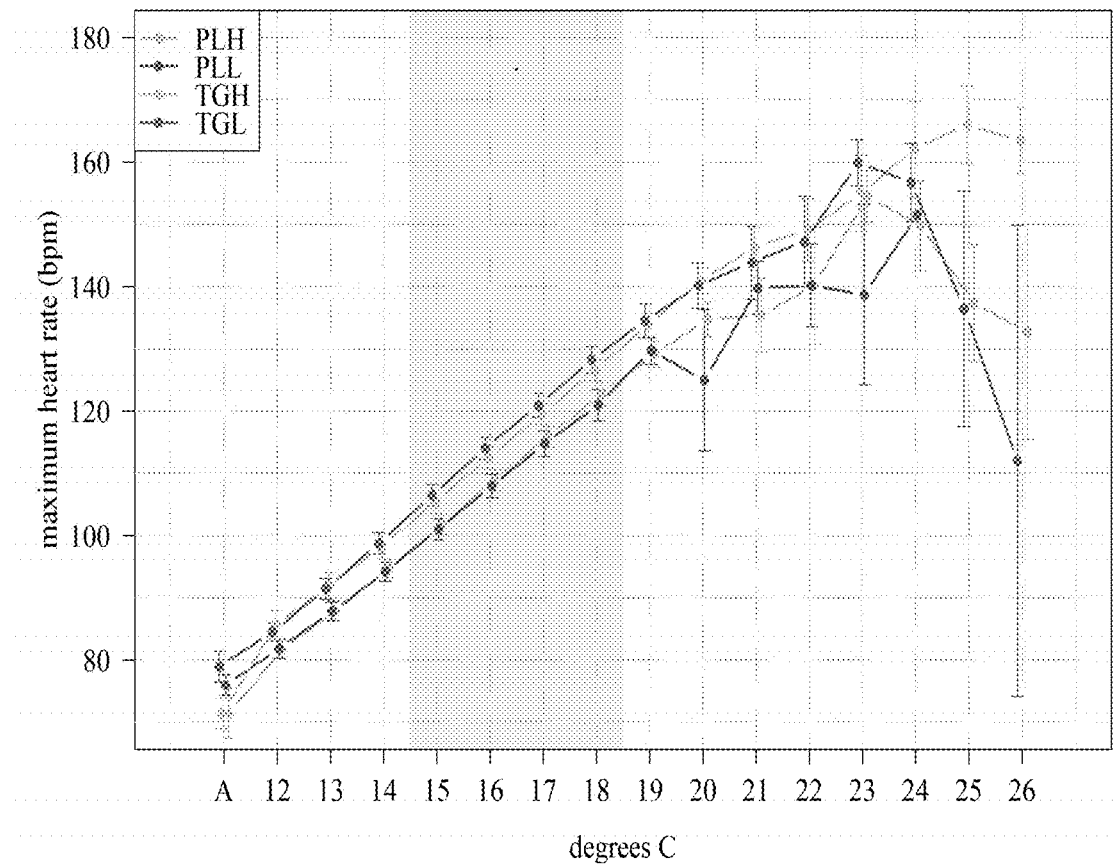
FIG. 10: Temperature dependent maximum heart rate test of diet groups after 8 weeks. Data are average heart rate (n=9)±SEM. Temperatures are shown on x-axis (A denotes atropine injection), heart rates in bpm on y-axis.

Maximum heart rate test was performed on nine fish (equal weight and length) per group at termination. FIG. 10 shows that the average heart rate was lower for PL vs TG diets from 14.5-18.5° C., hence an effect of lipid source and not EPA/DHA dose. The lower heart rate of PL diets could reflect either a higher cardiac output, stroke volume and/or ventricle mass (higher RVM to body length for PLH).

Figure 11:
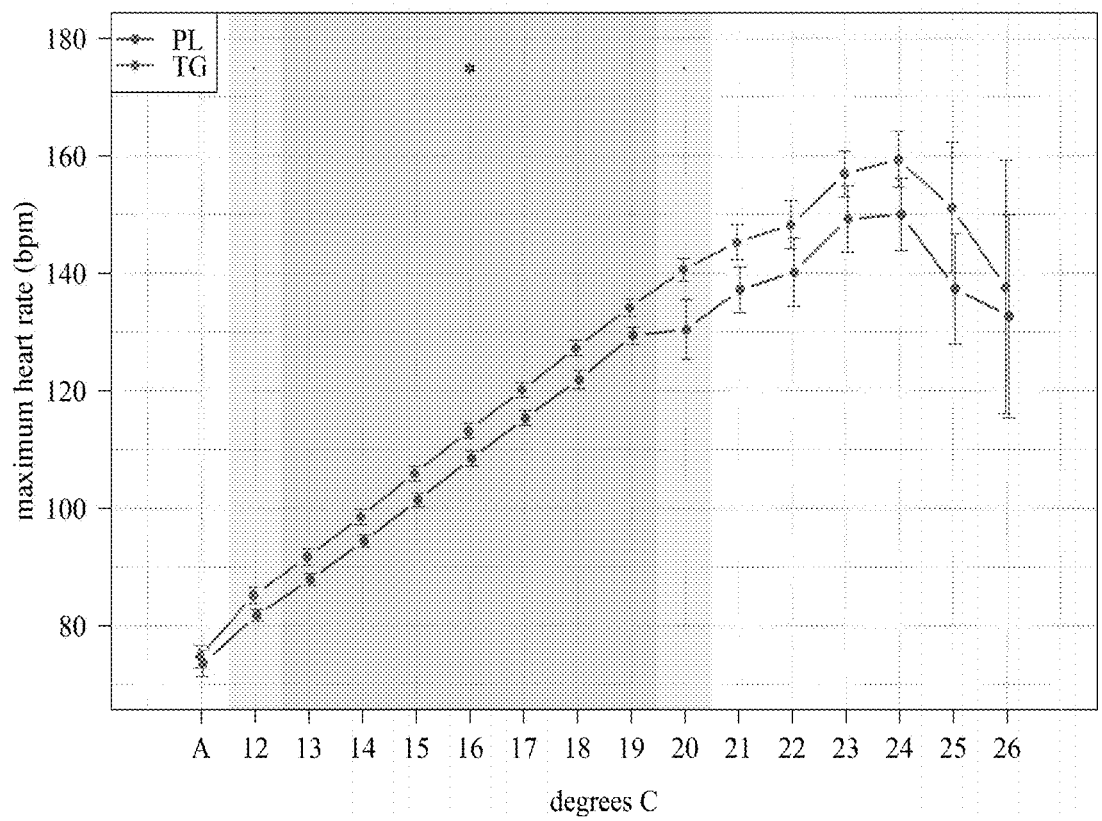
FIG. 11: Same as FIG. 10 but with combined heart rate values for the contrast diets PL and TG (high and low doses merged). Asterix and shaded area indicate temperatures with significantly different rates between PL and TG.

With the PL and TG diets combined, the rate differences were significantly different from 13-19° C. (FIG. 11). As commonly observed, maximum heart rates and arrhythmia temperature (AT) were reflecting the average heart rates in the linear area ($Q_{10}$>1.9), with lower rates resulting in lower max rates and AT (data not shown). All groups had similar optimum temperatures for aerobic scope (18° C., data not shown).

Heart Morphometry

Figure 12:
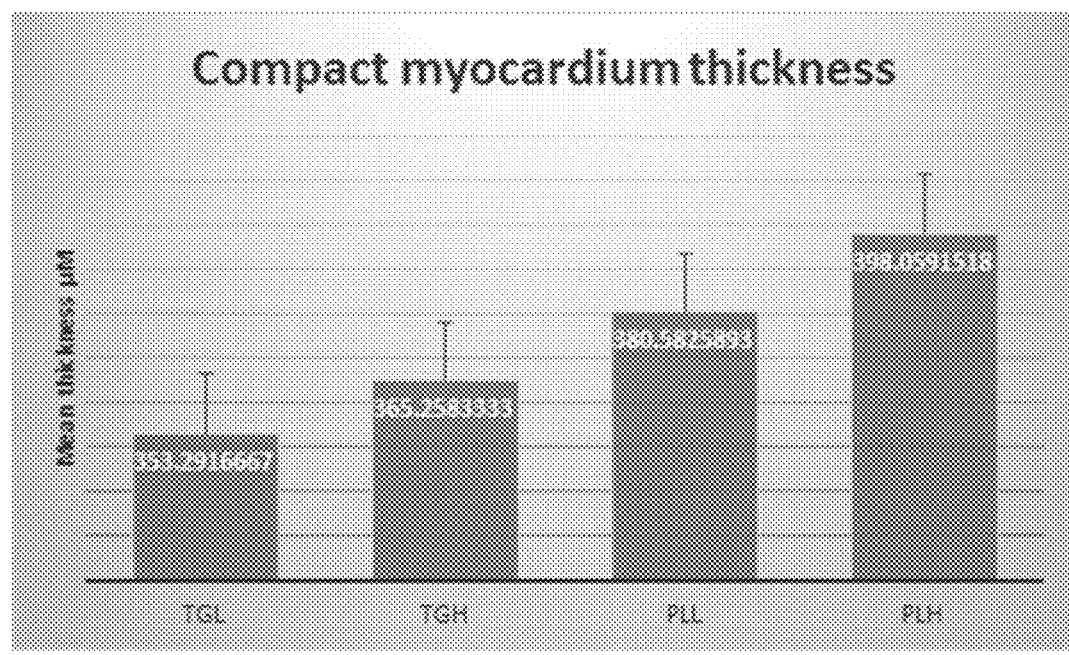
FIG. 12: Thickness of the compact myocardium for each diet after 8 weeks. Bars show average thickness (n=16) in μM from 8 measured data points along the ventricle±SEM.

The dietary effects on compact myocardium thickness (FIG. 12) were evaluated in 16 fish per diet group (n=8 per tank) sampled after 8 weeks feeding (end sampling). These were the same fish analysed for cardiac fatty acid composition.

Results indicate a trend of increased thickness of the compact myocardium according to diet lipid source (phospholipid vs triglyceride) and EPA/DHA dose (high vs low). These differences may explain the observed differences in heart rates between phospholipid and triglyceride diets. Results from other studies suggest that a thicker compactum relates to increased contraction efficiency and cardiac output, which further corresponds to a lower heart rate. PLH had 8 and 11% thicker compactum compared to respectively TGL and TGH. Pairwise post-hoc test (Tukey's) gave p=0.09 between PLH and TGL. Pairwise t-test without adjustment showed p=0.02 for PLH vs TGL and p=0.09 for PLH vs TGH. Presumably, data would have been significant by increasing the number of data points per section or number of fish measured.

Correlations

A correlation test was performed using the following factors recorded for individual fish per diet group: Body mass (W) and length (L), condition factor (CF), heart indices (ventricle mass and mass relative to W (RVMw) and L (RVMI)), compact myocardium thickness (CompTh), and selected heart fatty acid levels and sum/ratios (complete data in Appendix 3).

Figure 13:
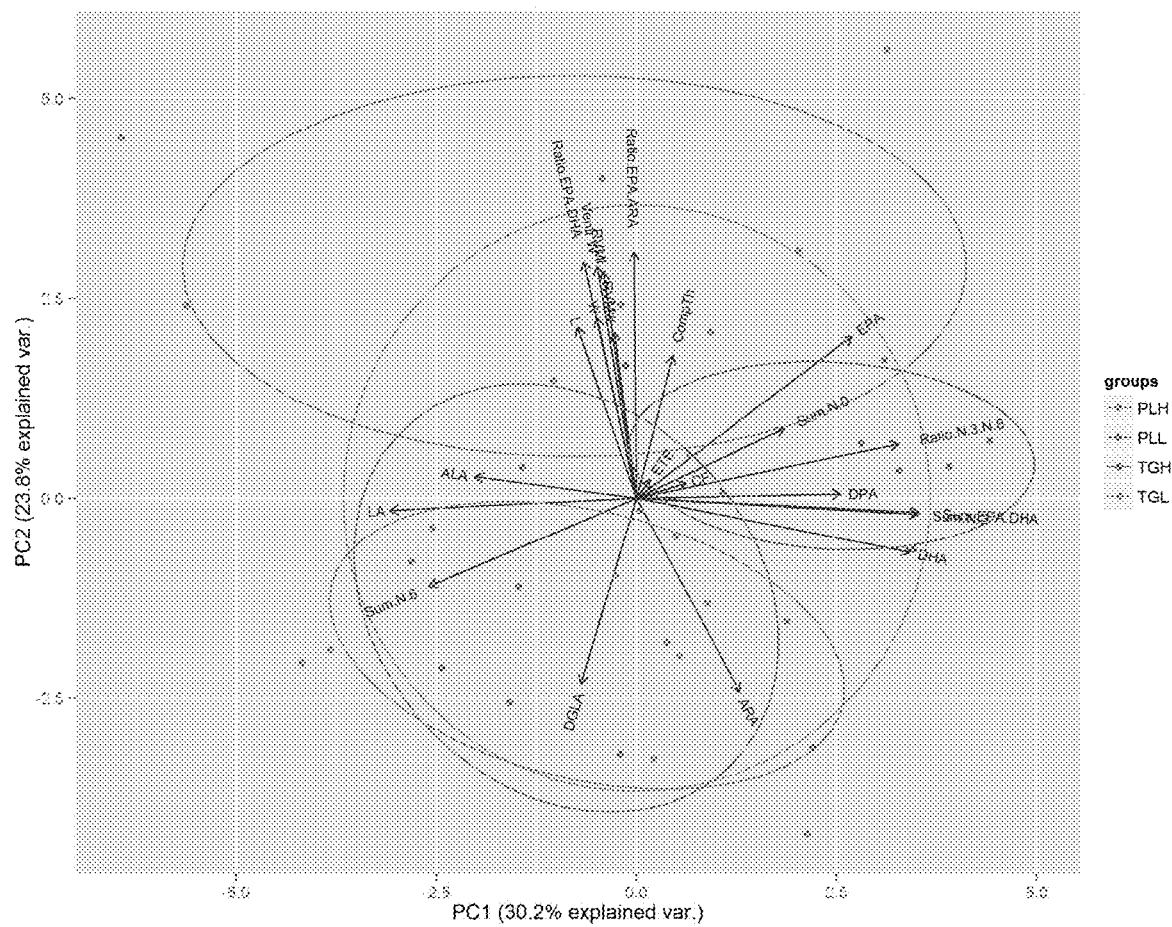
FIG. 13: PCA plot showing separation of diet groups according to several factors indicated in the plot and specified in the body text.
Figure 14:
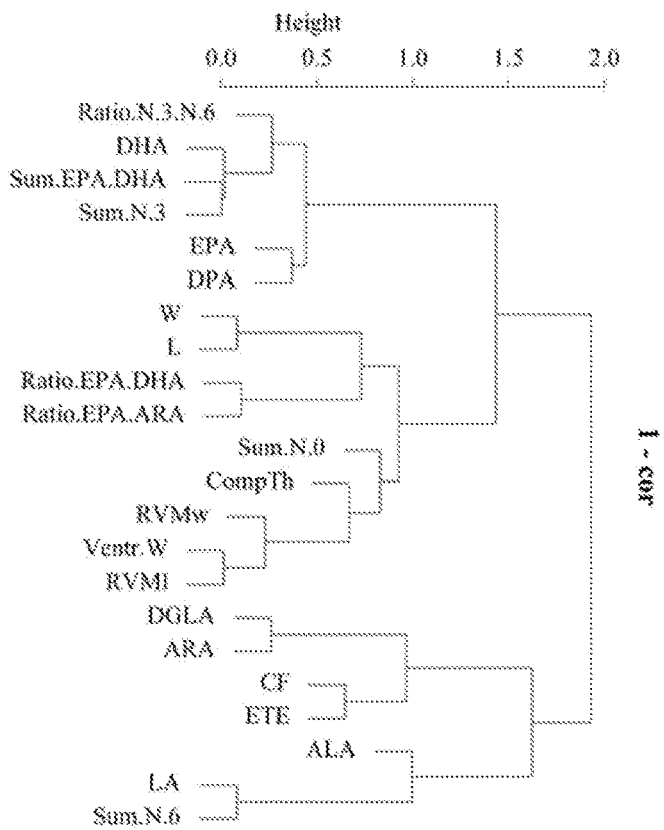
FIG. 14: Hierarchical clustering of different factors according to strength of correlation. Height on x-axis indicate level of correlation, i.e. lower number implies stronger correlation. Left panel: positive correlations and right panel: positive and negative correlations are treated equally based on R^2 values.
Figure 14:
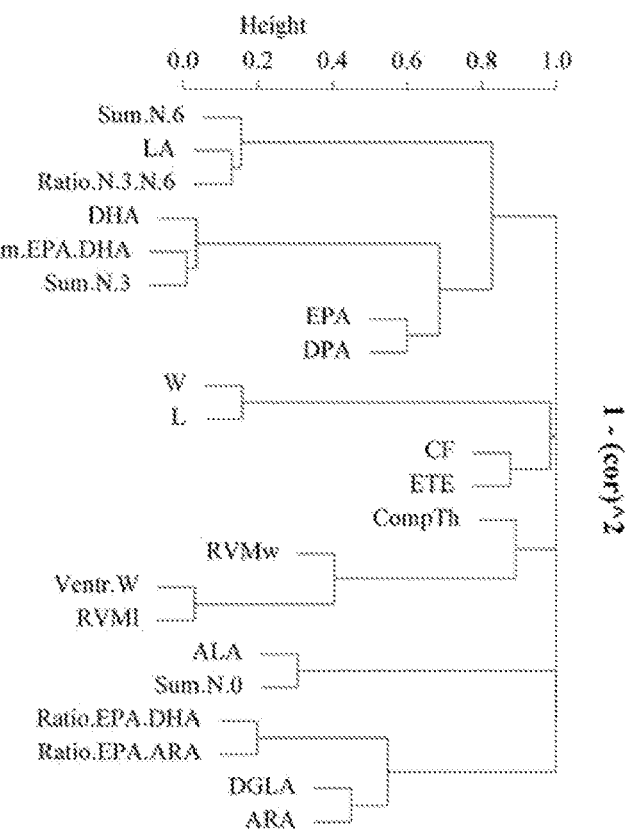

Principal component analysis indicate separation of diet groups and the factors explaining the separation (FIG. 13). The plot shows that PLH separates from the other groups due to body mass/length, CompTh, RVM and EPA levels and EPA/DHA and EPA/ARA ratios. The other groups separate according to their different levels of other cardiac fatty acids. PLL and TGL cluster together with different levels of mainly n-6 fatty acids, and TGH according to sum of n-3/EPA+DHA and n-3/n-6 ratio. TGH is partly overlapping with PLH according to EPA levels. Correlation values among the factors clustered according to positive (FIG. 14, left panel) and both positive and negative correlations (FIG. 14, right panel). Clustering of factors was generally as expected (e.g. W/L and heart indices). Among clustered fatty acid factors, strongest correlations were between EPA/ARA-EPA/DHA ratio, DHA-sum EPA+DHA-sum N-3 FAs, LA-sum N-6 and DGLA-ARA.

All publications and patents mentioned in the above specification are herein incorporated by reference. Various modifications and variations of the described compounds, compositions, methods and uses of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the biological and fishery sciences are intended to be within the scope of the following claims.

What is claimed is:

1. A method of improving a parameter of heart health fish comprising:
    feeding fish a dietary ration comprising an amount of krill meal effective to improve one or more parameters of heart health in said fish, wherein the ration has a fatty acid content and from 2% to 10% of the fatty acids in the ration are eicosapentaenoic acid (EPA) and docosahexaenoic acid (DHA) combined and the ratio of EPA to DHA is from 0.7 to 1.8.

2. The method of claim 1, wherein said one or more parameters of heart health are selected from the group consisting of one or more of improved cardiac fatty acid composition, improved erythrocyte fatty acid composition, increased rate of growth, increased body mass, increased body length, increased ventricle mass relative to body mass, increased ventricle mass relative to body length, improved swimming capacity, decreased maximum heart rate, and increased thickness of the compact myocardium.

3. The method of claim 2, wherein said improved cardiac fatty acid composition and erythrocyte fatty acid composition comprises an increase in levels of linoleic acid (LA, 18:2n-6) and/or alpha-linolenic acid (ALA).

4. The method of claim 1, wherein said ration is a pelleted ration.

5. The method of claim 1, wherein said ration comprises from about 4% to 15% krill meal.

6. The method of claim 1, wherein said ration comprises approximately 185-220 mg/g fatty acids and approximately 23-26% lipids.

7. The method of claim 6, wherein from 3-7% of the fatty acids in said ration are EPA and DHA combined.

8. The method of claim 6, wherein the ratio of EPA to DHA in said ration in between approximately 0.9 and 1.4.

9. The method of claim 1, wherein said fish are infected with a viral disease.

10. A method of improving a parameter of heart health in fish comprising:
    feeding fish a pelleted dietary ration comprising an amount of krill meal effective to improve one or more parameters of heart health quality in said fish, wherein said one or more parameters of heart health are selected from the group consisting of one or more of improved cardiac fatty acid composition, improved erythrocyte fatty acid composition, increased rate of growth, increased body mass, increased body length, increased ventricle mass relative to body mass, increased ventricle mass relative to body length, improved swimming capacity, decreased maximum heart rate, and increased thickness of the compact myocardium, wherein the ration has a fatty acid content and from 2% to 10% of the fatty acids in the ration are eicosapentaenoic acid (EPA) and docosahexaenoic acid (DHA) combined and the ratio of EPA to DHA is from 0.7 to 1.8.

11. The method of claim 10, wherein said improved cardiac fatty acid composition and erythrocyte fatty acid composition comprises an increase in levels of linoleic acid (LA, 18:2n-6) and/or alpha-linolenic acid (ALA).

12. The method of claim 10, wherein said ration is a pelleted ration.

13. The method of claim 10, wherein said ration comprises from about 4% to 15% krill meal.

14. The method of claim 10, wherein said ration comprises approximately 185-220 mg/g fatty acids and approximately 23-26% lipids.

15. The method of claim 14, wherein from 3-7% of the fatty acids in said ration are EPA and DHA combined.

16. The method of claim 10, wherein said fish are infected with a viral disease.

* * * * *